(12) United States Patent
Reed

(10) Patent No.: US 10,470,916 B1
(45) Date of Patent: Nov. 12, 2019

(54) PATIENT SAFETY DEVICE

(71) Applicant: Sherrell Marcia Reed, Madison, AL (US)

(72) Inventor: Sherrell Marcia Reed, Madison, AL (US)

( * ) Notice: Subject to any disclaimer, the term of this patent is extended or adjusted under 35 U.S.C. 154(b) by 0 days.

(21) Appl. No.: 15/489,556

(22) Filed: Apr. 17, 2017

Related U.S. Application Data

(60) Provisional application No. 62/324,690, filed on Apr. 19, 2016.

(51) Int. Cl.
*A61F 5/37* (2006.01)
*A61B 5/11* (2006.01)
*A61B 5/00* (2006.01)

(52) U.S. Cl.
CPC .......... *A61F 5/3769* (2013.01); *A61B 5/1115* (2013.01); *A61B 5/702* (2013.01); *A61B 5/6887* (2013.01)

(58) Field of Classification Search
CPC .... A61F 5/3769; A61F 5/3776; A61B 5/1115; A61B 5/702; A61B 5/6887
USPC .......................................................... 5/494
See application file for complete search history.

(56) References Cited

U.S. PATENT DOCUMENTS

| | | | | |
|---|---|---|---|---|
| 892,047 A * | 6/1908 | Halterman | ............... | A47G 9/04 128/872 |
| 2,640,996 A * | 6/1953 | Davis | .................... | A61G 1/013 5/626 |
| 2,912,977 A * | 11/1959 | Holbrook | ............... | A61F 5/3784 340/568.1 |
| 3,181,180 A | 5/1965 | Moore | | |
| 3,241,161 A * | 3/1966 | Dashosh | ............... | A47G 9/0261 383/66 |
| 3,601,824 A * | 8/1971 | Bradford | .................. | A61G 1/01 5/628 |
| 4,074,375 A | 2/1978 | Kella | | |
| 4,488,544 A * | 12/1984 | Triunfol | ................ | A61F 5/3784 128/871 |
| 4,653,131 A | 3/1987 | Diehl | | |
| 4,742,821 A | 5/1988 | Wootan | | |
| 4,852,587 A * | 8/1989 | Share | ......................... | A61F 5/37 128/869 |
| 4,853,996 A * | 8/1989 | Harrigan | ............... | A61F 5/3776 128/873 |
| 4,895,171 A * | 1/1990 | Onik | ...................... | A61F 13/00 128/869 |
| 5,027,456 A | 7/1991 | Wadsworth | | |

(Continued)

FOREIGN PATENT DOCUMENTS

CN 102579179 A 7/2012
CN 203183102 U 9/2013

*Primary Examiner* — Nicholas F Polito
*Assistant Examiner* — Rahib T Zaman
(74) *Attorney, Agent, or Firm* — Bradley Arant Boult Cummings LLP; Timothy L. Capria

(57) ABSTRACT

A safety device for restraining a person includes a fabric bottom panel, at least two fabric top panels, at least two side separable fasteners, and a top separable fastener. The fabric bottom panel is dimensioned to extend lengthwise along an underside of a mattress. The fabric top panels extend approximately lengthwise along the fabric bottom panel. Each side fastener attaches one of the at least two fabric top panels with the fabric bottom panel. The top separable fastener attaches the at least two fabric top panels to one another.

20 Claims, 9 Drawing Sheets

(56) References Cited

U.S. PATENT DOCUMENTS

| | | | |
|---|---|---|---|
| 5,070,557 A | | 10/1991 | Vincent et al. |
| 5,094,251 A | | 3/1992 | Miller |
| 5,425,381 A | * | 6/1995 | Peterson ............... A61F 5/3792 |
| | | | 128/876 |
| 5,623,950 A | | 4/1997 | Bergeron |
| 5,787,526 A | | 7/1998 | Smith et al. |
| 8,215,313 B1 | * | 7/2012 | Waltz .................... A61F 5/3715 |
| | | | 128/849 |
| 2004/0060113 A1 | * | 4/2004 | Lantagne ............. A47C 21/022 |
| | | | 5/494 |
| 2007/0261170 A1 | * | 11/2007 | Hollander ............ A44B 19/301 |
| | | | 5/636 |
| 2008/0115270 A1 | * | 5/2008 | McCarthy ................ A47G 9/02 |
| | | | 5/494 |
| 2013/0042386 A1 | * | 2/2013 | Montgomery ....... A47D 15/008 |
| | | | 2/102 |
| 2013/0312198 A1 | * | 11/2013 | Kelly .................. A47D 15/008 |
| | | | 5/655 |

* cited by examiner

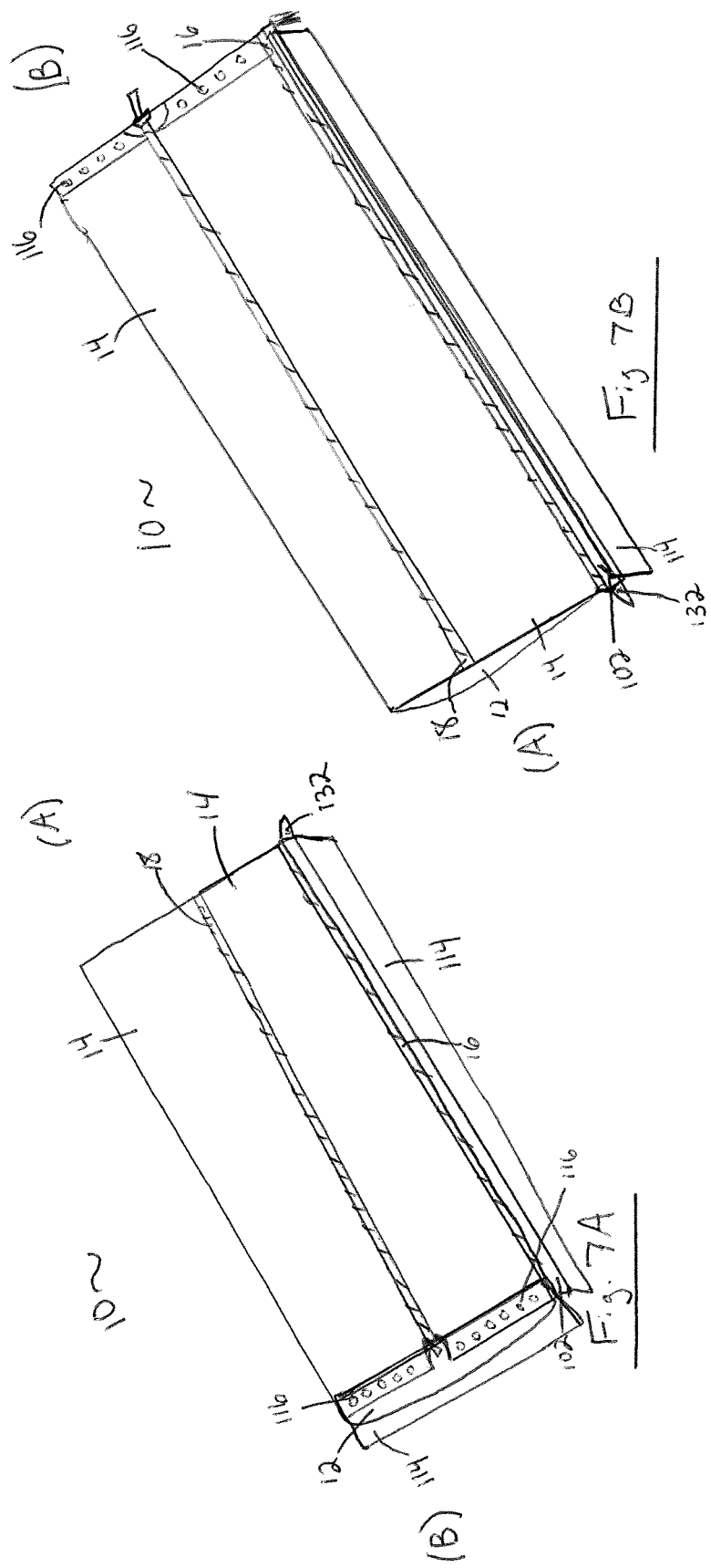

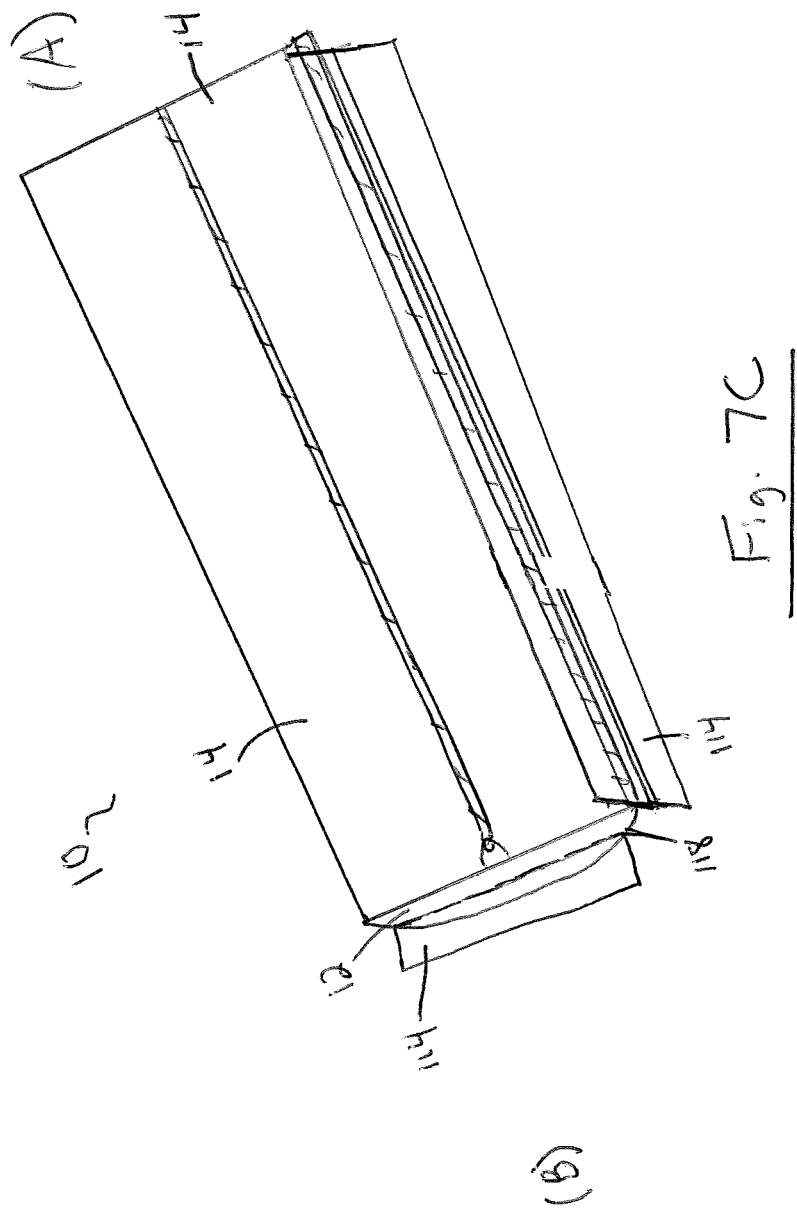

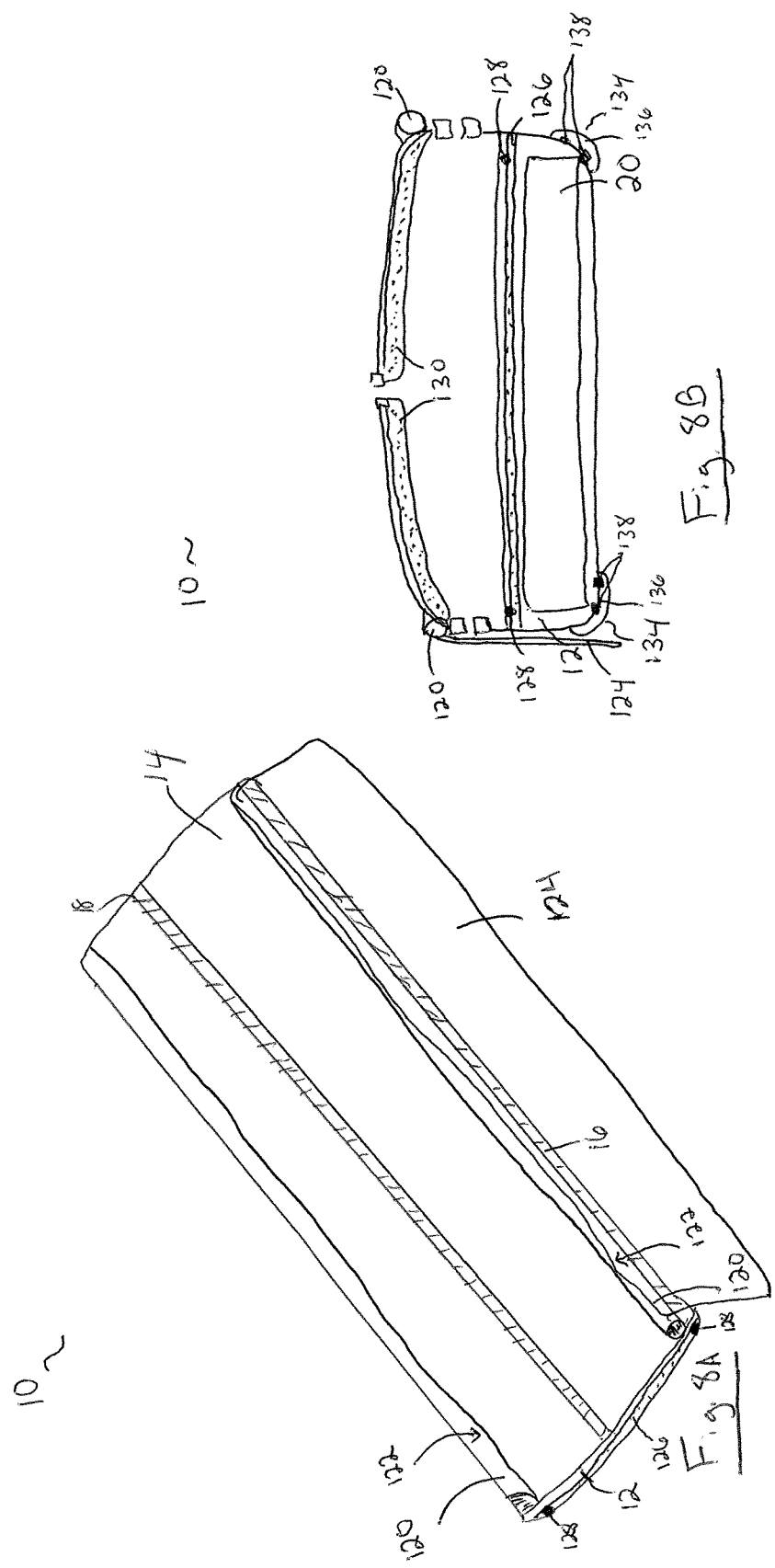

PATIENT SAFETY DEVICE

CROSS-REFERENCE TO RELATED APPLICATIONS

This application claims the benefit of U.S. Provisional Application No. 62/324,690, filed Apr. 19, 2016, which is incorporated herein by reference in its entirety.

BACKGROUND OF INVENTION

Various patient safety devices currently exist, and to an extent, these devices allow a caregiver to passively restrain a patient in a hospital bed, reducing the possibility that the patient might fall from the bed. These devices take many forms, with some including features to envelop the hospital bed mattress as well as the attached side rails, while others include structures that provide access to the patient, such as buckles, zippers, or straps. However, these devices do not provide the ability to access the patient from multiple angles. Often, the devices only provide one access point such that the caregivers cannot safely access the patient from various angles, and the access points are not constructed in a way that prevents a confused patient from being able to manipulate them. In addition, some devices utilize fasteners that would not allow caregivers quick access to the patient in the event of an emergency. Therefore, there exists a long-felt need in the art for a device capable of passively restraining a patient in a hospital bed, while allowing multiple, quick access points to the patient that are constructed in such a way as to prevent the patient from being able to release them.

BRIEF DESCRIPTION OF DRAWINGS

It should be noted that identical features in different drawings are shown with the same reference numeral.

FIG. 7A shows a left side perspective view of one embodiment of the present invention.

FIG. 7B shows a right side perspective view of the embodiment shown in FIG. 7A.

FIG. 7C shows a left side perspective view of another embodiment of the present invention.

FIG. 8A shows a side perspective view of yet another embodiment of the present invention.

FIG. 8B shows a cross-sectional view of the embodiment shown in FIG. 8A.

DETAILED DESCRIPTION

A patient safety device has been developed. The present invention is intended for the passive restraint of patients in a bed, while still allowing the patient to move comfortably on the bed and within the device. The device provides a caregiver peace of mind, knowing there is a reduced risk of the patient's accidental fall from the bed. Often, a patient may be disoriented or confused, thinking that he or she can get up unassisted, while in reality the patient's unassisted attempt to get up could result in a fall and potential injury. Therefore, the present invention also contemplates fasteners structured in such a way as to prevent the patient from being able to unfasten the device. However, the present invention also provides safe, quick access to the patient from multiple angles in the event of an emergency situation. Moreover, the present invention has a variety of applications, including in hospitals, home care, or childcare settings.

Figure 1:
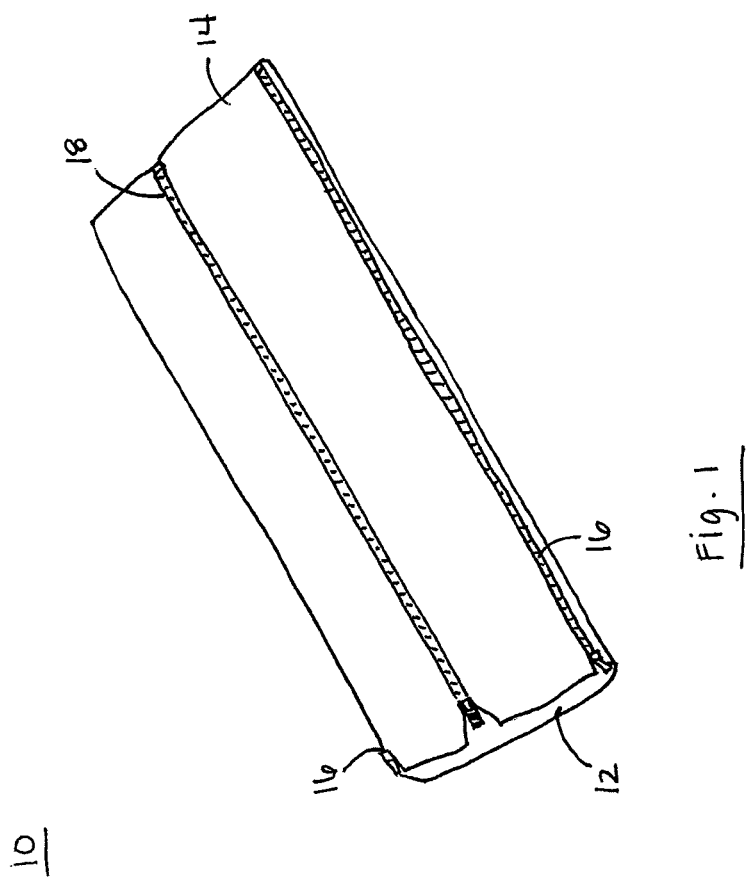
FIG. 1 shows a front perspective view of one embodiment of the present invention.
Figure 2:
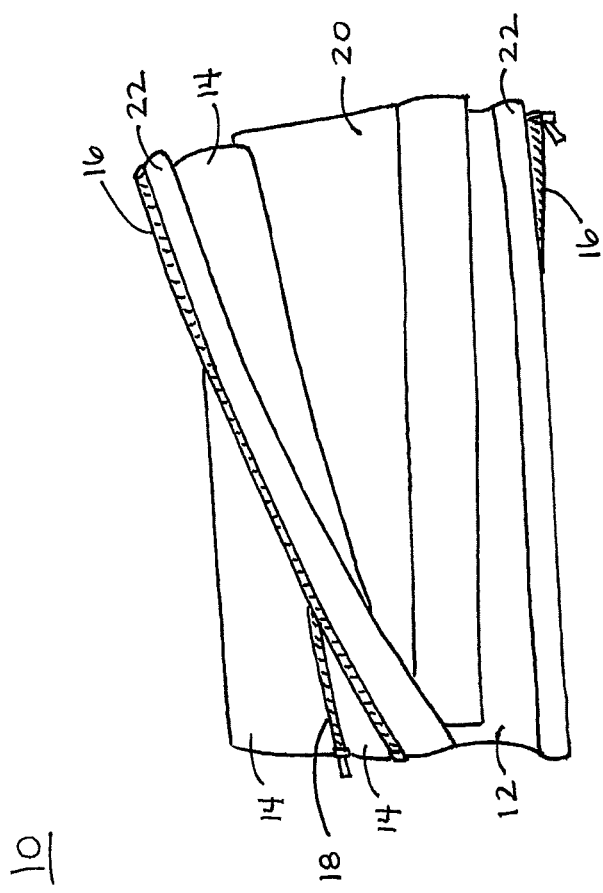
FIG. 2 shows a side perspective view of one embodiment of the present invention, shown with an unzipped side zipper.
Figure 3:
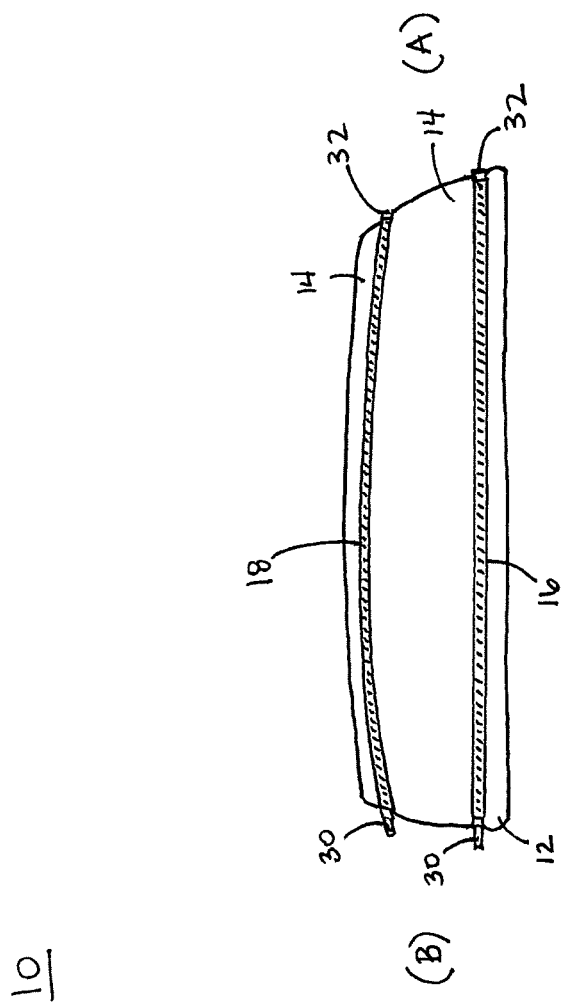
FIG. 3 shows a side perspective view of one embodiment of the present invention.
Figure 4:
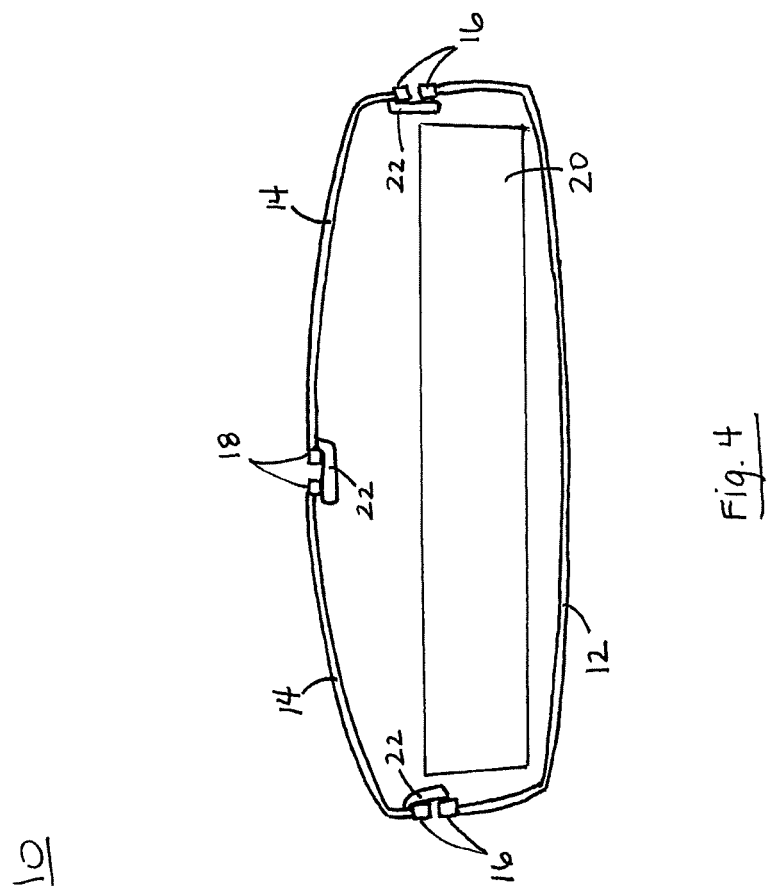
FIG. 4 shows a cross-sectional view of one embodiment of the present invention.

One embodiment of the patient safety device 10 is depicted in FIGS. 1 through 4. FIG. 1 shows some of the basic elements of the present invention. In this embodiment, the device 10 includes a bottom panel 12, which may be a large, flat piece of material that extends lengthwise along the underside of a mattress (not shown). The bottom panel 12 may be wide enough to extend beyond the underside of the mattress (not shown) and have enough fabric remaining to extend upward on both sides, as shown in FIG. 4. The bottom panel 12 may be comprised of any number of materials, including but not limited to fabric or flexible plastic. In a preferred embodiment, the bottom panel 12 may be made of a strong but flexible fabric.

As seen in FIG. 1, the device 10 also includes at least two top panels 14, which may extend approximately the same length as the bottom panel 12, however in any event, the top panels 14 are not meant to cover the patient's head or face (not shown). The top panels 14 may be made of any number of materials, similar to the bottom panel 12 as discussed above. The top panels 14 are positioned above the mattress (not shown) and patient (not shown), so that the mattress and patient are both enveloped within the device 10. As a result, and in a preferred embodiment, the top panels 14 may be made of a flexible, breathable fabric. In warmer climates, a user may prefer that the top panels 14 be made of a lightweight, breathable fabric. Alternatively, in colder climates or as preferred by the patient, the top panels 14 may be made of a heavier fabric that provides the added benefit of warmth for the patient. The present invention contemplates that the bottom panel 12 may be made of the same or different material than the top panels 14.

The device 10 includes a top zipper 18 that is positioned in the center of the device 10. This top zipper 18 runs lengthwise along the top side of the device 10, allowing the caregiver to unzip the device 10 and access the patient (not shown). Although a preferred embodiment includes the use of a zipper, the present invention contemplates the use of other types of fasteners, such as ties, straps, laces, buckles, snaps, buttons, hook-and-loop fasteners, and the like.

Additionally, as seen in FIG. 1, the device 10 includes at least two side zippers 16 that are positioned on either side of the mattress (not shown) and patient (not shown). The side zippers 16 also run lengthwise along the device 10, similar to, and parallel to, the top zipper 18 described above. In some situations, a caregiver may need to access a patient from one side or the other, and the additional zippers allow easier access. In other situations, a patient may need to exit the bed from one side or the other in order to move to different areas of the room. Again, the use of side zippers 16 in the present invention allows a patient to do so more easily than through the use of a top/center opening alone. Similar to the top zipper 18 described above, the embodiment shown utilizes zippers for the side zippers 16, but the present invention also contemplates the use of other types of fasteners in place of a zipper.

While the embodiment shown includes the use of one top zipper 18 and two side zippers 16, the present invention contemplates the use of any number or combination of top zippers 18 and side zippers 16. As a result, the present invention contemplates any number or configuration of bottom panels 12 and top panels 14 as well.

FIG. 2 shows one embodiment of the present invention in an unzipped configuration. One of the side zippers 16 is shown unzipped, so that the corresponding top panel 14 is pulled aside to expose the mattress 20 within. In this manner, the patient (not shown) would be able to exit the bed with the assistance of the caregiver. Alternatively, the caregiver would be allowed access to the patient on one side in order to administer treatment.

FIG. 2 also shows the padding flap 22 on the inside of the top panel 14, which provides protection to a patient from the inside of the device 10 by covering the side zipper 16. This padding flap 22 covers the zipper from the inside when the device 10 is in a zipped configuration, and prevents abrasions or other injury that may be caused by a patient rubbing against the zipper from the inside.

FIG. 2 shows an additional padding flap 22 for the same side zipper 16, located on the bottom flap 12. The present invention contemplates that each zipper may have only one padding flap 22, or may have more than one padding flap 22 on either side of the zipper for added protection. The padding flap 22 may be made of any number of materials, including the same type of material as the top panels 14 or bottom panel 12. In a preferred embodiment, the padding flap 22 may be an additional flap of material that is attached to the underside of the top panel 14 and which runs the entire length of the side zipper 16, forming an enclosure. Further, there may be a type of soft filling (not shown) inserted into the enclosed area of the flap material, which provides an added buffer between the patient and the side zipper 16. Alternatively, the padding flap 22 may not contain any filling, but instead may be multiple layers of fabric which cover the zipper from the inside.

FIG. 3 shows a side view of one embodiment of the present invention, with the top zipper 18 and side zipper 16 in a closed configuration. An added benefit of the device 10 is the positioning of the top zipper 18 and side zippers 16 in a manner such that the patient himself is unable to manipulate them. The end of the device 10 terminating at (A) as shown in FIG. 3 is intended to be the end corresponding with a patient's head (not shown). The end of the device 10 terminating at (B) as shown in FIG. 3 is intended to be the end corresponding with a patient's feet (not shown). As a result and in a preferred embodiment, the zipper stops 32 will be located at the "top" end of the device 10, that is, the end (A) meant to correspond to a patient's head (not shown). Conversely, when in a closed or fastened configuration, the zipper pull tabs 30 will be located at the "bottom" end of the device 10, that is, the end (B) meant to correspond to a patient's feet (not shown). This positioning of the top zipper 18 and the side zippers 16 will allow a caregiver to maintain easy access to a patient, but will hinder or prevent a patient from manipulating the zippers himself.

FIG. 4 shows a cross-sectional view of one embodiment of the present invention. In this embodiment, the device 10 includes a bottom panel 12 for positioning underneath a mattress 20, and two top panels 14 for positioning over both a mattress 20 and the patient (not shown). It can be seen that the device 10 is not meant to be uncomfortably restrictive. Instead, the device 10 leaves room for a patient (not shown) to move comfortably and naturally while lying in the bed, and is intended to be akin to a snugly-fitting blanket.

In use of the device 10, a caregiver may choose to unfasten the top zipper 18 if treatment is needed while the patient remains on the bed. Alternatively, a caregiver may choose to unfasten either of the side zippers 16 in order to access either side of the patient's body, or to allow the patient to get out of the bed in a safe, assisted manner. In some instances, such as with a patient who has suffered a stroke, the patient may have a weaker side, so the advantage of having a side zipper 16 on either side allows a caregiver to tailor the device 10 to a specific patient's needs.

Additionally, the added benefit of the padding flaps 22 can be seen in FIG. 4. As discussed above, there may be one padding flap 22 per zipper, as shown in FIG. 4. Alternatively, there may be multiple padding flaps 22 per zipper, depending upon user preference. The padding flap 22 may be fixed to one side of the zipper itself, or it may be fixed to the inside of the top panel 14 or bottom panel 12, adjacent to the corresponding zipper. In use of the device 10, when the zippers are in a closed configuration, the padding flaps 22 reposition such that they are in between the patient (not shown) and the zipper. In this manner, the padding flaps 22 cover the zipper and help to protect the patient from injury, such as pressure sores, that may result from rubbing against the inside of the zipper.

While the device 10 is shown as having an open end at the bottom, the present invention contemplates that there could be an additional flap of material (not shown) that joins the bottom panel 12 with the bottom ends of the top panels 14. This additional flap may provide added stability and strength to the device 10.

Additionally, the device 10 is shown as fitting around a mattress 20 and patient (not shown), and accordingly may be made in a wide variety of shapes and sizes. Depending upon the intended use, a small version may be made to assist a young child with the transition from a crib to a bed with no side rails. Similarly, alternate shapes and sizes may be used to tailor the device 10 to a hospital bed, or a bed in a home setting. The device 10 may also have alternate configurations in order to be used with a wheelchair, a seat within a vehicle, or even an infant carrier.

Figure 5:
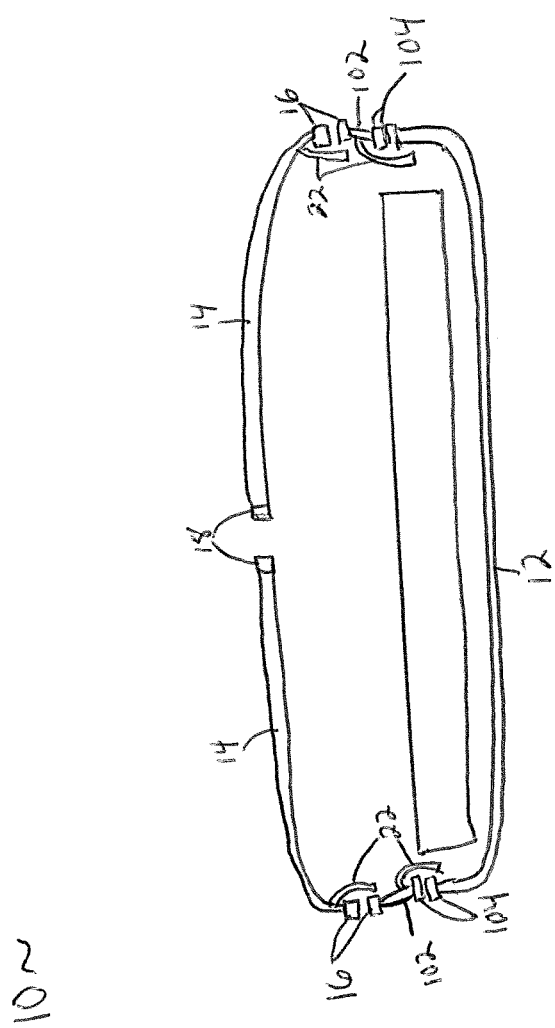
FIG. 5 shows a cross-sectional view of an embodiment of the present invention.

As shown in FIG. 5, in some embodiments of the device 10, a lateral panel 102 may extend downwardly from each of the side zippers 16 to the bottom panel 12. The lateral panels 102 may be dimensioned such that they extend downwardly beyond both sides of the mattress 20 when the device 10 is in use with the mattress 20. A lateral panel side zipper 104 may be disposed on each of the lateral panels 102 and extend lengthwise along the device 10 parallel to zippers 16. Advantageously, zippers 104 enable the device to be coupled with and uncoupled with the mattress 20 conveniently such that, for example, the lateral panel side zippers 104 can be disengaged, allowing the bottom panel 12 can remain under the mattress while disconnecting the top panels 14. The top panels 14 can be interchangeable and washable. This feature allows the mattress 20 and the bottom panel 12 to remain in-place when the top panels are replaced, cleaned, or interchanged between heavy weight for cold and light weight fabrics for warm temperatures or patient preference. The lateral panel side zippers 104 may be covered by an additional fabric flap 22 in the interior of the device 10.

Figure 6:
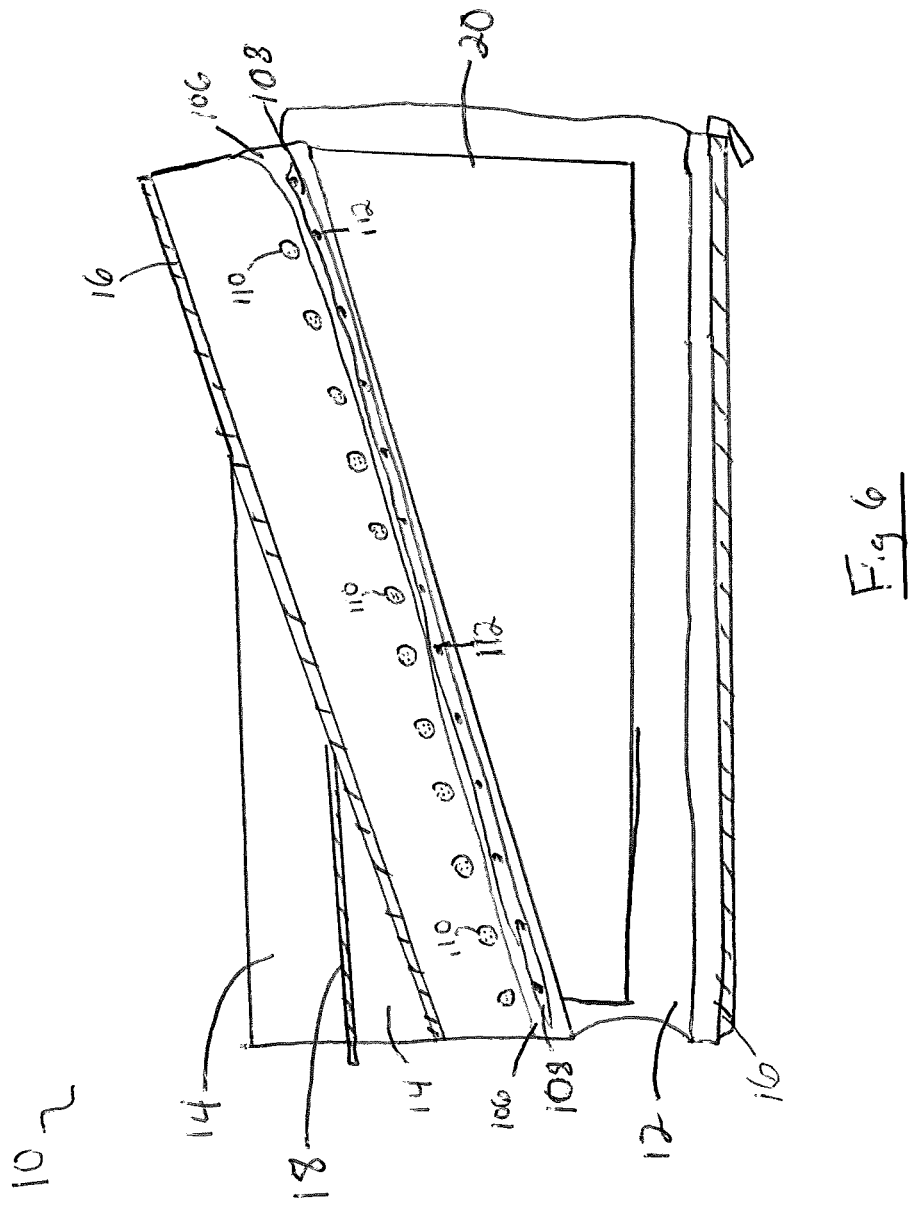
FIG. 6 shows a side perspective view of one embodiment of the present invention, shown with an unzipped side zipper.

As illustrated in FIG. 6, the device 10 may include fabric extending from the side zipper 16 that comprises a stretchable fastener feature 106, such as buttonhole elastic 108 and at least one button 110, extending lengthwise along the device 10. The stretchable fastener feature 106 may be disposed on either side, or both sides, of one or both of the side zippers 16. In embodiments of the device 10 having buttonhole elastic 108 and the at least one button 110, the buttonhole elastic 108 has a plurality of button holes 112 extending lengthwise across the fabric such that the buttons 110 can be variably fastened in the button holes 112 of the buttonhole elastic 108. This stretchable fastener feature 106 allows the device 10 to expand and contract to the differing sizes of patients such that the device 10 is safely secured and attached to the bottom panel 12 and comfortable for the patient.

As shown in FIGS. 7A and 7B, some aspects of the device include a skirt 114 extending end (A) along each lateral sides of the device 10 and along the end (B) of the device 10. In some embodiments of the device 10, the skirt 114 does not extend along end (A), while other embodiments having the skirt 114 ending along end (A) (not shown). The skirt 114 may extend from, for example, the lateral panels 102 or from any portion of the side of the device 10. At end (B) of the device 10, the skirt 114 may extend from the top panels 14 and comprise skirt fasteners 116 that fasten with the bottom panel 12. Skirt fasteners 116 may be any suitable fastener, such as a snap button, a zipper, sewing, or any fastener described herein. As shown in FIG. 7C, the skirt fastener 116 may fasten with the bottom panel 12 at an interior edge 118 of the bottom panel 12. The skirt fastener 116 may laterally extend along end (B) of the top panels 14 and the bottom panel 12. The skirt 116 may also function such as to retain attachment of the top panels 14 to the device 10 when the side zippers 16 are in the unzipped position, which allows for the mattress 20 to be exposed with the top panels 14 remaining attached toward the end (B) of the device 10.

The skirt 114 and skirt fastener 116, when in the fastened position, prevent the patient from exiting the device bed from end (B) of the device 10 (i.e., exiting the bed from the patient foot end of the mattress). This feature is particularly advantageous when the patient may be confused or disoriented to prevent the patent from exiting from end (B) of the device 10. The type of skirt fastener 116 used may vary based on patient risk. For example, a light duty skirt fastener 116, such as snaps, can be used where patient is at a low risk of an unassisted exit of the device 10 to allow for more patient movement, while a heavy duty skirt fastener 116, such as a zipper, may be used where the patient is at a high risk of an unassisted exit of the device 10 to reduce the risk of an unassisted bed exit. In embodiments where the heavy duty skirt fastener 116 is a zipper, the zipper may be a separating zipper on each of an interior edge 118 of the bottom panel 12 and an interior edge of the top panels 14.

As shown in FIGS. 8A and 8B, some embodiments of the device 10 include a bumper 120 extending from one or, or both, lateral sides of the device 10. The bumper 120 be provided into the interior sides of top panels 14 to decrease the risk of the patient rolling off from either side of the mattress 20, reducing the risk of an unintentional exit from the device 10 by the patient. Further, the bumpers 120 prevent the patient from rolling off either side of the mattress 20 and becoming trapped between a side of the mattress 20 and the lateral sides of the device 10. The bumper 120 may have a generally cylindrical shape such that no hard corners are formed to further reduce risk of injury to the patient. The bumper 120 may be surrounded by a bumper cover 122, which may be constructed of the same, or different, materials or fabrics of which other components, such as top panels 14, are constructed. The bumper cover 122 may be sewn onto to or integrally formed with the top panels 14. The bumper cover 122 may include an extra bumper panel 124 that extends beyond the top and the bottom of the mattress 20.

The bumper panel 124 may be fastened by any suitable fastener, such as zippers, ties, straps, laces, buckles, buttons, or hook-and-loop fasteners, to the interior sides of the bottom panel 12 such as to anchor the top panels 14 to the top and the bottom of the device 10 while still allowing the middle of the mattress 20 to be visible.

The device 10 may include and be configured to receive a removable pad 126 towards the bottom of the device 10 yet over the mattress 20. The pad 126 may be water proof, washable, and compatible to the size and the width of the mattress 20 so that the pad can be periodically replaced, such as when soiled by the patient. The pad 126 may be secured by pad fasteners 128, which can be any of the fasteners discussed herein, such as snaps. The pad fasteners 128 may be positioned at positions around the mattress to removably attach to the underside of the pad 126 and/or the bumper panel 124 such that they are out of reach to a patient secured by the device 10. In one embodiment, the pad fasteners 128 are located at or proximate to each of the four corners of the device 10. A top replaceable pad 130 may be attached to, coupled with, or inserted into the underside of top panels 14 so as to prevent soiling of the top panels 14.

Various features may be added to improve the aesthetics of the device, such as a fabric tab 132 (shown in FIGS. 7A and 7B) that extends toward end (A) from the side zipper 16 that is dimensioned to generally hide mattress 20 from view when the device 10 is coupled with the mattress 20. The tab 132 may have a triangular profile. Further, ornamental buttons may be placed on the exterior of the device 10, such as on the tab 132, to enhance the appearance of the device.

In an embodiment of the device 10, at least one expansion feature 134 may allow the device 10 to be expanded and contracted to securely receive patients of differing sizes while maintaining patient comfort. The at least one expansion feature 134 may comprise an expansion panel 136 of fabric with expansion fasteners 138, such as snaps or zippers, having alternate positions such that the at least one expansion feature 134 can be in a contracted position and an expanded position. The expansion feature 134 may be attached to or integrally formed with the bottom panel 12 and positioned at each of the lateral sides of ends A and B of the device 10. The expansion fasteners 138 may be located on the bumper panel 124 (not shown), and may be positioned along the length (i.e., between end (A) and end (B)) to correspond with expansion or contraction of the expansion panel 136 to the size of each individual patient, while still maintaining stability to the mattress 20 and a secure attachment to the bottom panel 12.

While the invention has been described with respect to a limited number of embodiments, those skilled in the art, having benefit of this disclosure, will appreciate that other embodiments can be devised which do not depart from the scope of the invention as disclosed here.

What is claimed is:

1. A safety device for restraining a person, comprising: a fabric bottom panel dimensioned to extend and be disposed lengthwise from the person's feet up to the person's head and at least along the entire width along an underside of a mattress; at least two fabric top panels extending approximately the entire length along the fabric bottom panel, wherein the at least two fabric top panels are configured and dimensioned to be disposed above a mattress; at least two side releasable fasteners, each releasable side fastener attaching one of the at least two fabric top panels with the fabric bottom panel; and a top releasable fastener attaching the at least two fabric top panels to one another, wherein each of the at least two releasable fasteners and the top releasable fastener is releasable from itself.

2. The safety device of claim 1, wherein each of the two side releasable fasteners and the top releasable fastener comprise a zipper.

3. The safety device of claim 1, wherein the fabric bottom panel and the at least two fabric top panels define an interior, and wherein a padding flap is disposed in the interior over at least one of the at least two side releasable fasteners or the top releasable fastener.

4. The safety device of claim 3, wherein the interior is dimensioned to substantially receive a person.

5. The safety device of claim 1, wherein the at least two side releasable fasteners extend lengthwise from a first end to a second end.

6. The safety device of claim 5, wherein each of the at least two side releasable fasteners comprises a zipper including a zipper pull tab, the zippers configured such that the zipper pull tabs are located at the second end when the zippers are in a fastened position.

7. The safety device of claim 5, wherein the first end is dimensioned to receive a head of the person, and the second end is dimensioned to receive feet of a person.

8. The safety device of claim 5, wherein the first end, the second end, or both the first end and the second end, is open to the interior.

9. The safety device of claim 5, wherein the second end comprises an additional fabric flap joining the bottom panel and each of the at least two top panels.

10. The safety device of claim 1, wherein the safety device is configured for restraining a child.

11. The safety device of claim 1, wherein the fabric body panel and the at least two fabric top panels together are configured to loosely secure a person over the mattress.

12. The safety device of claim 1, wherein the fabric bottom panel and the at least two fabric top panels define an interior, and wherein at least two padding flaps are disposed in the interior over at least one of the at least two side releasable fasteners or the top releasable fastener.

13. The safety device of claim 12, wherein the at least two padding flaps are fixed to at least one of the at least two side releasable fasteners or the top releasable fastener.

14. The safety device of claim 12, wherein the at least two padding flaps are fixed to bottom panel or one of the at least two top panels, each padding flap disposed in the interior adjacent to one of the at least two side releasable fasteners or the top releasable fastener.

15. A safety device for restraining a person, comprising: a fabric bottom panel dimensioned to extend lengthwise from the person's feet up to the person's head and at least entirely widthwise along an underside of a mattress; at least two fabric top panels configured and dimensioned to be disposed above a mattress, the fabric top panels extending at least the entire length along the fabric bottom panel; at least two side zippers, each side zipper attaching one of the at least two fabric top panels with the fabric bottom panel and extending from a first end to a second end, wherein each of the first end and the second end are open; a top zipper attaching the at least two fabric top panels to one another; and an interior defined by the fabric bottom panel and the at least two fabric top panels.

16. The safety device of claim 15, wherein the at least two fabric top panels are of substantially equal dimensions.

17. The safety device of claim 15, wherein each of the two fabric top panels are constructed of a lightweight, breathable fabric.

18. The safety device of claim 15, wherein each of the two fabric top panels are constructed of a heavy fabric.

19. The safety device of claim 15, wherein the at least two side zippers and the top zipper extend parallel to one another.

20. The safety device of claim 15, wherein a padding flap is disposed and secured over each of the at least two side zippers and the top zipper.

\* \* \* \* \*